United States Patent [19]

Ophir et al.

[11] Patent Number: 5,143,070

[45] Date of Patent: Sep. 1, 1992

[54] TRANSAXIAL COMPRESSION TECHNIQUE FOR SOUND VELOCITY ESTIMATION

[75] Inventors: Jonathan Ophir; Youseph Yazdi, both of Houston, Tex.

[73] Assignee: The University of Texas Systems Board of Regents, Austin, Tex.

[21] Appl. No.: 438,695

[22] Filed: Nov. 17, 1989

[51] Int. Cl.$^5$ .............................................. A61B 8/00
[52] U.S. Cl. .................... 128/660.01; 73/597
[58] Field of Search ............... 128/660.02, 660.06, 128/660.01; 73/597, 703

[56] References Cited

U.S. PATENT DOCUMENTS

| | | | |
|---|---|---|---|
| 2,894,595 | 7/1959 | Brown | 73/597 |
| 3,942,381 | 3/1976 | Brown et al. | 73/703 |
| 4,244,226 | 1/1981 | Green et al. | 73/717 X |
| 4,361,154 | 11/1982 | Pratt, Jr. | 128/660 |
| 4,383,533 | 5/1983 | Bhagat et al. | 128/660.01 |
| 4,434,661 | 3/1984 | Miwa et al. | 73/625 |
| 4,492,117 | 1/1985 | Chubachi | 73/597 |
| 4,566,460 | 1/1986 | Soto et al. | 128/660.01 |
| 4,580,574 | 4/1986 | Gavish | 128/660 |
| 4,669,482 | 6/1987 | Ophir | 128/660 |
| 4,702,258 | 10/1987 | Nicholas et al. | 128/660 |
| 4,716,765 | 1/1988 | Hirama | 73/626 |
| 4,745,808 | 5/1988 | Hagen | 73/597 |
| 4,781,199 | 11/1988 | Hirama et al. | 128/660.01 |
| 4,805,622 | 2/1989 | Riedlinger et al. | 128/660.06 |
| 4,807,635 | 2/1989 | Ophir | 128/660.01 |

FOREIGN PATENT DOCUMENTS

| | | |
|---|---|---|
| 0099764A1 | 2/1984 | European Pat. Off. |
| 0152874A1 | 8/1985 | European Pat. Off. |
| 0221409A2 | 5/1987 | European Pat. Off. |
| 0256686A1 | 2/1988 | European Pat. Off. |
| WO87/17494 | 12/1987 | PCT Int'l Appl. |

OTHER PUBLICATIONS

J. Ophir, et al., Optimization of Speed-of-Sound Estimation from Noisy Ultrasonic Signals, Jan. 1989, IEEE Transactions on Ultrasonics, Ferroelectrics, and Frequency Control, vol. 36, No. 1, pp. 16-24.

N. Hayashi, A New Method of Measuring In Vivo Sound Speed in the Reflection Mode, Feb. 1988, J. Clin. Ultrasound 16, pp. 87-93.

J. Ophir and T. Lin, A Calibration-Free Method For Measurement of Sound, Speed and Biological Tissue Samples, Sep. 1988, IEEE Transactions on Ultrasonics, Ferroelectrics, and Frequency Control, vol. 35, No. 5, pp. 573-577.

D. E. Robinson, et al., Measurement of Velocity of Propagation From Ultrasound Pulse-Echo Data, 1982, Ultrasound in Med. & Biol., vol. 8, No. 4, pp. 413-420.

Konton Assios and Ophir, Variance Reduction of Speed of Sound Estimation in Tissues Using Beam Tracking Method, Sep. 1987, IEEE Transactions on Ultrasonics, Ferroelectrics, and Frequency Control, vol. UFFC-34, No. 5, pp. 524-530.

Kondo, et al., A Fundamental Evaluation of In Vivo Velocity Measurement by Crossed Beam Method, 1986, 2419, Japanese Journal of Applied Physics, vol. 25, Supplement 25-1, pp. 100-102.

*Primary Examiner*—Francis Jaworski
*Attorney, Agent, or Firm*—Arnold, White & Durkee

[57] ABSTRACT

An improved ultrasonic pulse-echo method and apparatus that has particular application in estimating sound velocity in organic tissue is disclosed. The method employs a standard transducer or transducer containing device which is translated transaxially, thereby compressing or displacing a proximal region of a target body in small known increments. At each increment, a pulse is emitted and an echo sequence (A-line) is acquired from regions within the target along the sonic travel path or beam of the transducer. Segments of the echo sequence corresponding to a distal region within the target are selected as a reference to estimate the incremental change in echo arrival time. A plot of these arrival time estimates versus the target compression depth is then generated and a least squares linear fit is made. The slope of the linear fit is $\hat{c}^{-1}$, where $\hat{c}$ is an estimate of the speed of sound in the target.

5 Claims, 4 Drawing Sheets

2

TRANSAXIAL COMPRESSION TECHNIQUE FOR SOUND VELOCITY ESTIMATION

This invention was made with government support under GRANT CA 38515 and CA 44389, amended by the National Institutes of Health. The government has certain rights in the invention.

BACKGROUND OF THE INVENTION

1. Field of the Invention

This invention relates generally to methods and apparatus for performing ultrasonic diagnosis of a target body. More particularly, the invention pertains to methods and apparatus for the measurement of sound speed in a target body. The invention is especially concerned with techniques for enhancing the accuracy of sound velocity measurements in compressible targets using one or more ultrasonic transducers in pulse-echo mode.

2. Description of Related Art

Traditional ultrasonic diagnosis is achieved by transmitting ultrasonic energy into a target body and generating an image from the resulting echo signals to survey anatomical structures. A transducer is used to both transmit the ultrasound energy and to receive the echo signals. During transmission, the transducer converts electrical energy into mechanical vibrations. Acquired echo signals produce mechanical oscillations in the transducer which are reconverted to electrical signals for amplification and recognition.

A plot or display (e.g., on an oscilloscope, etc.) of the electrical signal amplitude vs. echo arrival time yields the amplitude line (A-line) or echo sequence corresponding to a particular ultrasonic transmission. When the A-line is displayed directly as a sinusoidal pattern modulating at radio frequency (RF) it is referred to as an RF or "undetected" signal. For imaging, the A-line is often demodulated to a non-RF or "detected" signal.

Ultrasound techniques have been extensively used in the field of diagnostic medicine as a non-invasive means of analyzing the properties of tissue in vivo (i.e., living). A human or animal body represents a non-homogenous medium for the propagation of ultrasound energy. Acoustic impedance changes at boundaries of varying density and/or sound speed within a target body. A portion of the incident ultrasonic beam is reflected at these boundaries. Inhomogeneities within the tissue form lower-level scatter sites that result in additional echo signals. Images may be generated from this information by modulating the intensity of pixels on a video display in proportion to the intensity of echo sequence segments from corresponding points within the target body.

Conventional imaging techniques are widely used to evaluate various diseases within organic tissue. Imaging provides information concerning the size, shape and position of soft tissue structures using the assumption that sound velocity within the target is constant. Qualitative tissue characterization is carried out by interpretation of the grey scale appearance of the echograms. Qualitative diagnosis largely depends on the skill and experience of the examiner as well as system characteristics. However, images based only on relative tissue reflectivity cannot be used for a quantitative assessment of disease states.

Techniques for quantitative tissue characterization using ultrasound are needed for more accurate diagnosis of disease. One of the most promising parameters for quantitative measurement is sound speed. Speed of sound changes within regions of varying density and/or molecular compressibility within the tissue. Thus, it is expected that changes in tissue density due to disease will result in changes in the speed of sound. Indeed, it has been shown that changes in the speed of sound in tissue often correlate with tissue pathology. For example, cirrhotic liver tissue has been observed to contain more fat than normal liver tissue. The velocity of sound in cirrhotic tissue would therefore be expected to be lower than in normal tissue. Similarly, changes in tissue density in the region of tumors may result in changes in sound velocity in the tumor region. Unfortunately, however, such changes are relatively small and account for up to only 10% of the speed of sound in normal tissue. Therefore, accuracy in sound velocity estimation is extremely important in the analysis of tissue for pathological conditions. Usually, the accuracy of sound velocity estimations must be at least 1.0% to have specific value for quantitative tissue characterization. Hence, a need exists for the accurate measurement of sound velocity in organic tissue for clinical diagnosis.

Traditionally, measurement of sound speed has been conducted with transmission techniques. A first method of sound velocity measurement involves the transmission of sound pulses through tissue regions of known dimension and recording the time required for the pulse to traverse the region. The quotient of travel distance and travel time is computed to yield the velocity. However, due to the softness of most tissues, the dimensions of the tissue sample cannot be accurately measured which results in an error-prone measurement of sound velocity. Moreover, a reference liquid with a known speed of sound may be required to calibrate the apparatus.

A second transmission technique that has been used in medical diagnostics involves a transmitting transducer and a separate receiving transducer arranged so that they are aimed at one another with their respective axes of radiation coincident. The body of the subject is placed between the transmitting and receiving transducers. However, in vivo application of this technique has been limited to accessible organs like the breast or testes; other in vivo applications can be adversely affected by such factors as bowel gas, bone and inaccessibility.

A third transmission technique is disclosed by Ophir and Lin, "A Calibration-Free Method for Measurement of Sound Speed in Biological Tissue Samples", *IEEE Transactions on Ultrasonics, Ferroelectrics, and Frequency Control*, Vol. 35, No. 5, (1988) 573–577. This method allows accurate measurement of the speed of sound in soft tissue samples, while overcoming the limitations of initial techniques. The method employs a receiving hydrophone and a transmitting transducer that are coaxially aligned opposite each other. The transmitting transducer is in contact with the tissue sample, while the hydrophone penetrates the tissue sample at well-controlled incremental depths. The transit times of the pulse are recorded for all penetration depths of the hydrophone. These transit times are then plotted against the relative depths of the hydrophone, and a linear regression fit is made to the data. The slope of the fitted line is $\hat{c}^{-1}$, where $\hat{c}$ is the estimated speed of sound in the tissue sample. The technique requires neither calibration involving a reference medium, nor the knowledge of the thickness of the tissue sample. Yet, while this technique is capable of accurate measurements of tissue in vitro, it is clearly not suitable for speed of sound estimations in vivo.

Several techniques have been proposed for the measurement of sound velocity in vivo using ultrasonic transducers in pulse-echo mode. In one method, sound speed is measured using misregistration between pulse-echo images of the same structure obtained with two different sound beams. Sound velocity is determined from the difference in position of the same feature in different images. This method works best when a well-defined feature is available. In simulated tissue regions, known as "phantoms", thin wire added to the region will provide such a well-defined feature. However, well defined features are not easy to find in living tissue and the resulting sound speed measurement is therefore not as accurate. See Robinson et al., "Measurement of Velocity of Propagation from Ultrasonic Pulse-Echo Data", *Ultrasound in Med. & Biol.*, Vol. 8, No. 4, (1982) 413-320.

In another pulse-echo technique called the "focus adjustment method", the mean sound speed between a reflector and linear array transducer is measured using the following three parameters: time of flight, time of flight difference, and distance between two receiver elements. To detect time of flight, the system delay-line time compensator is adjusted to obtain the sharpest reflector image. Thus, the sharpness of the target is maximized by interactive user control of signal delays at the transducer aperture. However, irregular tissue structures cause random refractions of the ultrasonic beams and make sharp focusing difficult. Also, the method is highly dependent on qualitative judgment. See Hayashi et al., "A New Method of Measuring In vivo Sound Speed in the Reflection Mode", *J. Clin. Ultrasound*, Vol. 16, (1988) 87-93.

A third pulse-echo method described in U.S. Pat. No. 4,669,482, involves in vivo sound velocity estimation by identifying segments of different sound velocity along a tracked ultrasonic beam using at least two widely-separated acoustic vantage points. The tracked beam is partitioned into at least two contiguous segments, the boundary between the two segments being the inner body of the body wall fat. A plurality of ultrasound pulse travel time measurements are made, each with a different apparent angle of intersection between the tracked beam and the tracking beam. For each measurement, techniques are employed for correcting refraction occurring in a transverse plane. Data pairs collected in the plurality of measurements are fitted to an appropriate equation using curve-fitting techniques well known in the art, by which the index of refraction at the body wall inner boundary, the inclination of the inner boundary, and the speed of sound in the internal tissue are derived. This technique, however, is not desirable in clinical settings because of the large "footprint" of the apparatus on the patient that results in a cumbersome examination procedure. Also, inaccuracies due to bone and/or bowel gases are common because of the wide spacing between transmitting and receiving transducers.

Hence, all the above pulse-echo techniques are clinically limited due to the need to use two widely separated acoustic vantage points and/or by the requirement that an identifiable, discrete target be available in the tissue. The use of two widely separated vantage points makes the apparatus and the examination procedure cumbersome, while the existence of a discrete target cannot always be guaranteed. Another potential problem is due to the effects of the overlying fat layer of the body on the estimation.

SUMMARY OF THE INVENTION

The present invention provides an improved pulse-echo method and apparatus that has particular application in estimating sound velocity in organic tissue. The present invention addresses the problems of prior pulse-echo techniques by providing a relatively small footprint and obviating the need for a readily identifiable, discrete target within the tissue.

According to the present invention, a standard transducer or transducer containing device is translated transaxially, thereby compressing or displacing a proximal region of a target body in small known increments. At each increment, a pulse is emitted and an echo sequence (A-line) is acquired from regions within the target along the sonic travel path or beam of the transducer. Segments of the echo sequence corresponding to a distal region within the target are selected as a reference to estimate the incremental change in echo arrival time. A plot of these arrival time estimates versus the target compression depth is then generated and a least squares linear fit is made. The slope of the linear fit is $\hat{c}^{-1}$, where $\hat{c}$ is an estimate of the speed of sound in the tissue.

The present invention takes advantage of the acoustical properties of physically compressible or displaceable materials. These materials often contain a large number of acoustic "scatterers." These scatterers, being small compared to the wavelength of the sound frequencies involved, tend to reflect incident sound energy in all directions. For example, in homogeneous tissue regions, the scatterers may comprise a collection of nearly identical reticulated cells. The combined reflections from each scatterer create a background echo signal called speckle. The present invention employs standard pattern matching techniques to track a reference echo sequence segment corresponding either to a reflector or other echo source, such as speckle, in a distal tissue region within the target body. See, e.g., J. S. Bandat and A. G. Piersol, "Random Data: Analysis and Measurement Procedures," *Wiley Interscience*, New York 1971, pp. 30-31. A discrete reflector, like a bone or blood vessel, may be used as a reference if desired, but is not necessary; any arbitrary segment of the backscattered echo sequence may be used as a reference.

Bias occasioned by distal deformation of the reference echo source due to the proximal compression or displacement of the target may be corrected by using a second stationary transducer. The second transducer is oriented such that its beam intersects the beam of the first transducer at a small angle within the region of the reference echo source. The echo time delay due to the distal deformation is detected by the second transducer and is used to unbias the sound velocity estimate. While two acoustic vantage points are used, they are maintained at close proximity to each other, so that the total transducer "footprint" on the target is no larger than that which is due to a standard transducer array.

The present invention is of particular interest in interrogating organic tissue, especially human and other animal tissue. A principal object of such interrogation is to detect echo signals in the tissue that may suggest the presence of abnormalities. More specifically, the effect of compression or displacement of the tissue on the characteristics of the echo signals becomes a possible key to such detection. It will be noted at this point that the invention is contemplated to have significant applications other than in the study of tissue. One such application, for example, may be materials and products such as cheese or crude oil that are physically compressible or displaceable by movement of a transducer. Thus, as a transducer is pressed against such a material, particles within the material are displaced from one position to another. For elastic materials, release of the pressure enables the particles to return to their original position.

It will be noted that the transducers employed in the present invention need not be in direct contact with the materials to which they are applied. It is necessary, however, that transducers be sonically coupled to the materials. Sonic coupling methods and agents are well known in the art.

It will also be noted that a material may be interrogated according to the invention either (a) by advancing a transducer against a material to increase compression, or (2) by retracting a transducer from a compressed position within the material.

As noted above, it is not necessary that an echo from a discrete feature in a tissue or other compressible material be employed. It is sufficient that an identifiable echo segment be present in the echo signal resulting from a transmittal signal. Even though the physical feature within a material responsible for a selected echo sequence segment may not be clearly known, the selected echo segment is an adequate reference for the purposes of the invention. Thus, compression of the material and the signal travel times determined before and after such compression may be based on such echo segments.

As stated above, the invention may be practiced either by compressing a transducer against a compressible material from an initially non-compressed condition, or by retracting a transducer from an initially compressed condition. In either case, however, it is preferable that the distance traveled by the transducer be less than the wavelength of the ultrasonic signal produced or received by the transducer.

The present invention may also be employed for localized estimation of sound speed in targets having multiple layers. The speed of sound in each of progressively deeper layers is sequentially estimated by employing the same techniques discussed above. Distal regions at layer boundaries are used as the echo source for arrival time estimates. According to the present invention, the speed of sound can be estimated in each layer from only two echo sequences along the axis of radiation. Thus, imaging of the speed of sound parameter in a plane or volume of a target body can also be accomplished by appropriate lateral translation of the transducers.

Other objects and advantages of the invention will become readily apparent from the ensuing description.

BRIEF DESCRIPTION OF THE DRAWINGS

FIG. 1b shows a plot of the RF echo signal originating from the distal tissue region interrogated in FIG. 1a;

FIG. 2b shows a plot of the time shifted RF echo signal originating from the distal tissue region interrogated in FIG. 2a;

FIG. 3b shows a plot of the further time shifted RF signal from the tissue region interrogated in FIG. 3a;

DETAILED DESCRIPTION

The basic method resembles the penetrating hydrophone transmission technique discussed above. An adaptation of this technique to the pulse-echo mode is used. A transducer is positioned on or otherwise coupled to a target body and advanced axially toward the target in small known increments. As noted earlier, the invention may also be practiced by incrementally retracting a transducer from a previously compressed position. Since the relatively large aperture size precludes penetration of the tissue, small tissue compressions occur instead. At each increment, a pulse is emitted and echo sequence (A-line) segments from one or more selected distal tissue regions are used as a reference. Any arbitrary segment of the backscattered RF echo signal from within the tissue may be identified and used as a reference. The selected segment —wavelet—of the RF signal corresponds to a particular echo source within the tissue along the beam axis of the transducer. As the transducer compresses the tissue, it moves closer to the echo source, thereby shortening the travel path of the pulse and corresponding echo. The change in arrival times for echoes originating from the echo source as the transducer is incrementally advanced (or retracted) is related to the speed of sound in the tissue. Thus, the speed of sound may be determined even though the distance between the transducer aperture and the selected echo source are unknown.

The present invention contemplates transducers that may be piezoelectric, ferroelectric or magnetostrictive in nature. The present invention is not limited by the size, focusing properties or bandwidth of the transducer to be employed.

Figure 1A:
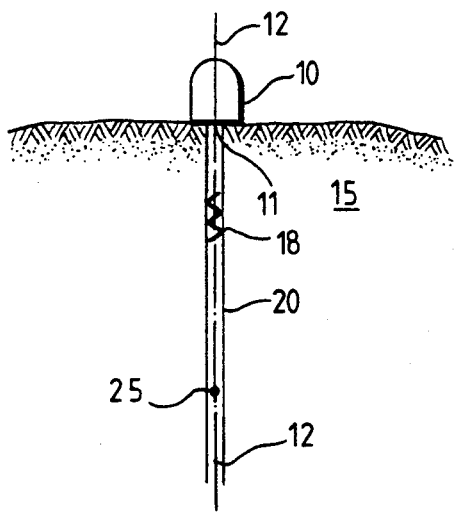
FIG. 1a shows an embodiment of the invention where one transducer is sonically coupled to a target body to interrogate a distal tissue region within the target body.
Figure 1B:
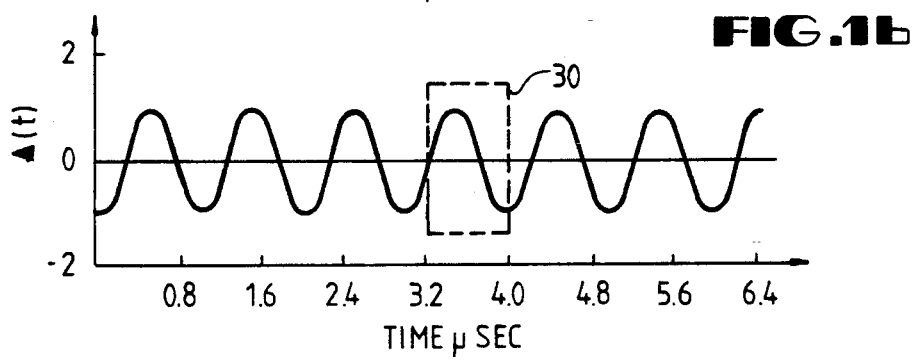

FIG. 1a shows the transducer 10 sonically coupled to a target body 15. An ultrasonic pulse 18 is shown propagating within beam 20 toward a echo source 25 on beam axis 12. As the pulse 18 propagates through the target 15, corresponding echoes are generated and arrival times noted at the transducer aperture 11. The combination of all echoes generated from reflections within the beam 20 is the echo sequence or A-line corresponding to pulse 18. A radio frequency ("RF") signal plot of the A-line acquired from pulse 18 is shown in FIG. 1b. The amplitude of the signal in millivolts is plotted against echo arrival times in microseconds ($\mu$s). Latter arrival times correspond to progressively deeper regions within the target body 15. An echo wavelet 30, within a chosen arrival time window, is selected as a reference. The time window may be selected based on anatomical data from ultrasound imaging, or may be arbitrary, e.g., every x micro seconds. The wavelet 30 originates from the echo source 25 that is at an unknown distance from the transducer aperture 11.

Figure 2A:
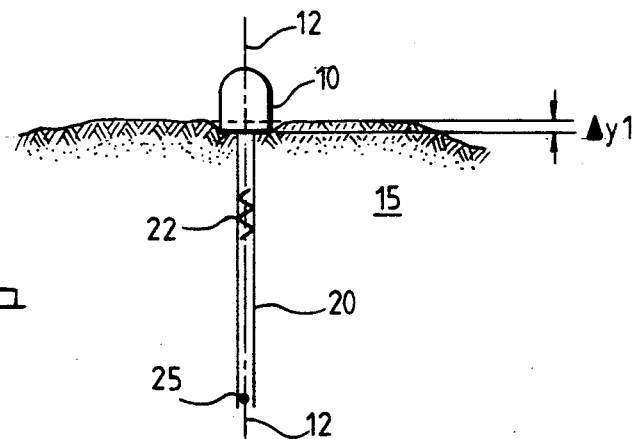
FIG. 2a shows the transducer of FIG. 1a imparting a small compression to a proximal region of the target body.
Figure 6:
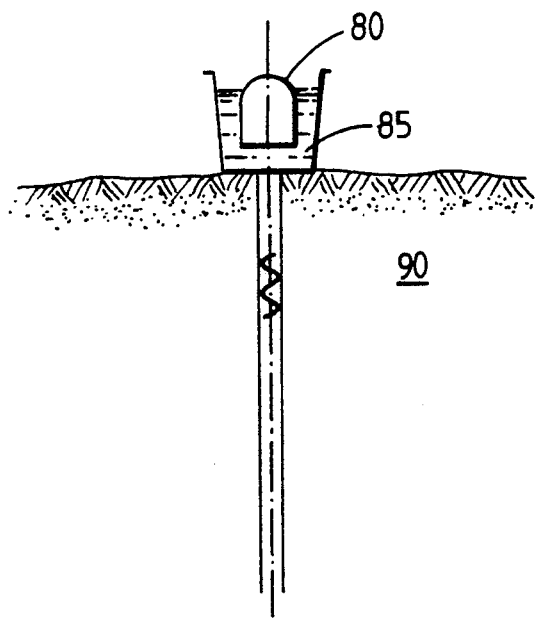
FIG. 6 shows an embodiment in which a transducer is sonically coupled to a target via a stand-off device containing an acoustic coupling fluid.

FIG. 2a shows the transducer 10 being translated along axis 12 to impart a small compression ($\Delta y_1$) to the tissue. Alternatively, as shown in FIG. 6, a transducer 80 may be associated with a stand-off device 85 which allows the transducer 80 to be acoustically or sonically coupled to the target body 90 without being in direct contact with the target body. In this case the stand-off 85, and not the transducer, compresses the target. In either case, however, the incremental compressions of the transducer or transducer containing device are dependent on the frequency of the transducer employed. More specifically, the magnitude of the incremental compressions are based on the wavelength which is a function of transducer frequency. In general, incremental shifts of less than about one wavelength are employed unless a discrete target is used as a reference. Otherwise, tracking the reference signal segment will be complicated by phase wrap. For example, in ophthalmic diagnosis a transducer of about 20 mHz may be employed, whereas a transducer of 3-5 mHz would be suitable for interrogating abdominal tissue. When a transducer of 3-5 mHz is used, the compressions are generally on the order of several mm, preferably between 0.1-2 mm.

Figure 2B:
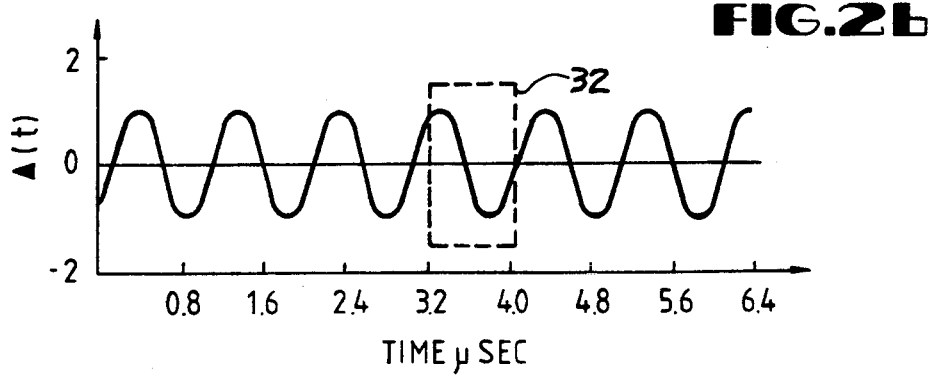

After the transducer 10 compresses the target, a second pulse 22 is emitted and the corresponding A-line segment is acquired from a desired depth within the tissue. FIG. 2b shows the RF plot of a time shifted A-line corresponding to pulse 22. The wavelet segment 32 associated with echo source 25 is also time shifted. The time shifted wavelet 32 is tracked within the selected time window using standard pattern matching techniques. The arrival time of wavelet 32 is prior to that of wavelet 30 above, since the distance between aperture 11 and feature 25 was shortened by the compression $Y_2$.

Figure 3A:
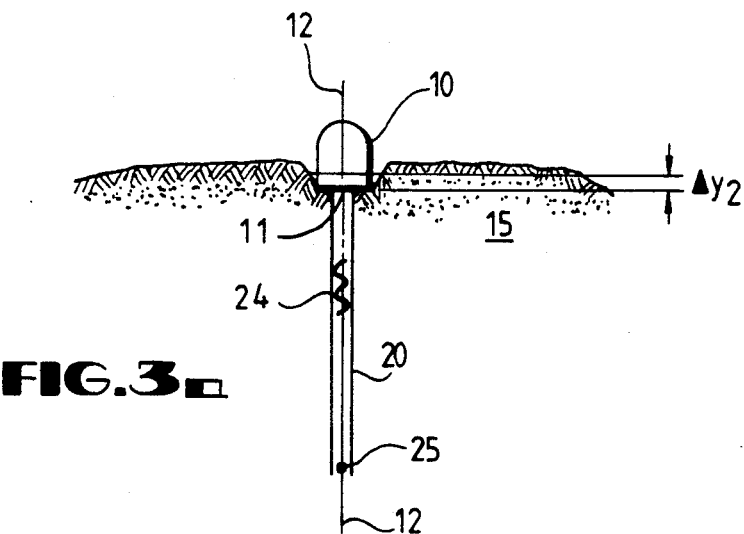
FIG. 3a shows the transducer of FIG. 1a imparting a further compression to a proximal region of the target body.
Figure 3B:
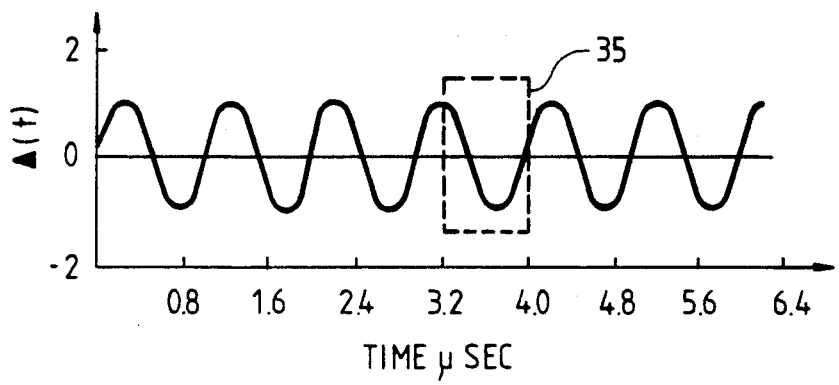

FIG. 3a shows further tissue compression ($y_1$) and a third pulse 24 emitted after the compression. The RF plot of the A-line in FIG. 3b shows an additional time shift in the signal. The wavelet 35 is tracked within the selected time window and is used to note the signal time shift. Assuming uniform sound speed and no displacement of the echo source involved in producing the RF signal wavelet of interest, the sound speed estimate in the tissue contained between the transducer and the location of these scatterers is:

$$\hat{c} = \frac{2}{n} \sum_{i=1}^{n} \frac{\Delta y_i}{\Delta t_i}, \quad (1)$$

where n is the number of uniform transducer compressional displacements, $\Delta y_i$ is the ith compression, and $\Delta t_i$ is the ith measured temporal shift in the reference echo signal wavelet. The factor of 2 in the numerator accounts for the pulse-echo nature of the technique in which ultrasound (pulses) travels to and returns (echoes) from the echo source in the selected distal region. However, the method of the present invention is not limited to a particular algorithm for calculating the sound speed characteristics of a target body.

According to the present invention, the one transducer embodiment discussed above may be conveniently employed in instances in which the target body being interrogated contains very compressible materials. Also, the method may be adapted to compress the tissue and acquire an A-line segment prior to the arrival of an elastic wave associated with the proximal compression. This is possible because, although the elastic wave travels at about 20 meters per second (m/s), the ultrasonic pulse travels at about 1540 m/s. Thus, the A-line is obtained from the selected time window prior to the arrival of the elastic wave. However, this is not feasible in some instances. In these cases, the assumption of no distal feature displacement is inadequate. Although the displacements of echo sources within the target will generally fall off asymptotically with range, minute displacements may occasionally be detected even far from the transducer. When this occurs, it is necessary to make a correction for the distal displacements.

To correct the estimate, the expression of eq. (1) is modified to reflect the presence of additional, unknown time delays $\Delta t_{d,i}$ due to such displacements indicated by the subscript d. Therefore, the resulting modified estimate of the speed of sound is:

$$\hat{c}_b = \frac{2}{n} \sum_{i=1}^{n} \frac{\Delta y_i}{\Delta t_i - \Delta t_{d,i}}. \quad (2)$$

Since the quantities ($\Delta t_i - \Delta t_{d,i}$) $\leq \Delta t_i$ are the actual time delays that are measurable, the estimate is always positively biased unless the $\Delta t_{d,i} = 0$.

Figure 4A:
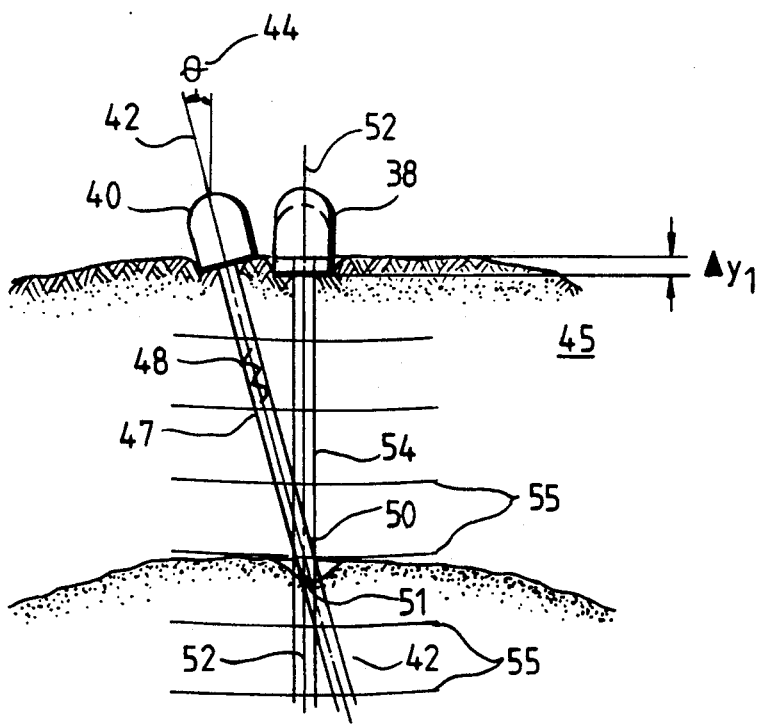
FIG. 4a shows an embodiment of the invention where both compressing and noncompressing transducers are acoustically coupled to a target body to interrogate a distal tissue region within the target body.

Fortunately, the quantities $\Delta t_{d,i}$ can be independently estimated using a second transducer. This is shown in FIG. 4a. In addition to the compressing transducer 38, a stationary noncompressing transducer 40 is used, whose beam axis 42 is directed such that it intersects the beam axis 52 of the compressing transducer 38 at the range that corresponds to the echo source 50. The noncompressing transducer 40 operates in the pulse-echo mode and detects minute displacements of the echo source 50 in the region of beam intersection that appear at time shifts $\delta t_{d,i}$. In a preferred embodiment, a pair of matched ultrasonic transducers is used for the compressing and noncompressing functions, respectively. Still, the invention also contemplates unmatched transducers, or the combination of a compressing transducer and a noncompressing steerable transducer array.

The beam of the noncompressing transducer may be oriented to intersect the beam of the compressing transducer in the region of the echo source of interest by using known beam tracking techniques. For example, the compressing transducer 38 may operate in pulse-echo mode and acquire echo sequence segments having a unique arrival time from echo source 50. The noncompressing transducer 40 can be spaced laterally from the first transducer to operate as a echo receiver. The noncompressing transducer 40 is angled until an echo burst coincident in arrival time with the desired echo source is received. The angle of orientation 44 is noted when the beams of both transducers intersect at the desired echo source 50.

Figure 4B:
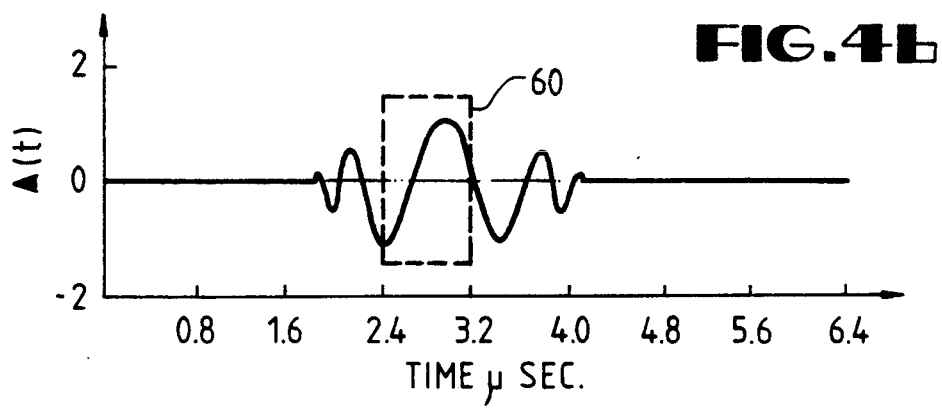
FIG. 4b shows a plot of the RF signal originating from the distal tissue region interrogated in FIG. 4a from the vantage point of the noncompressing transducer.
Figure 4C:
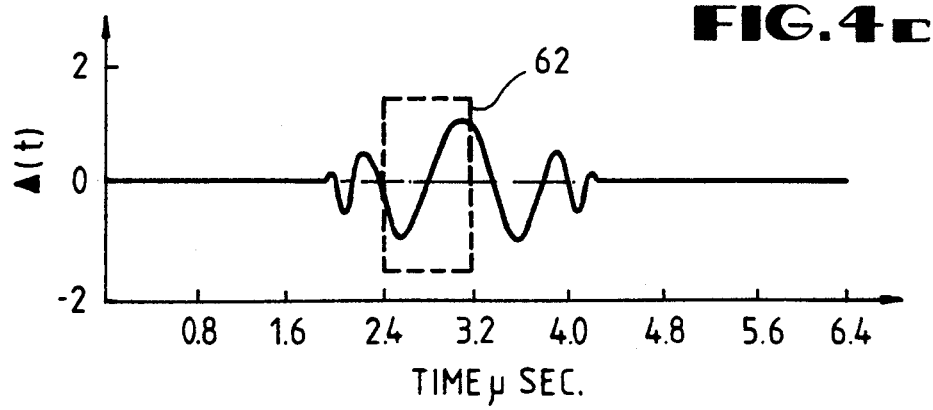
FIG. 4c shows a plot of a time shifted RF signal originating from the distal region interrogated in FIG. 4a; from the vantage point of the noncompressing transducer.

Continuing in FIG. 4a, the noncompressing transducer 40 emits a pulse 4s from the surface of the target 45. As pulse 48 travels through tissue regions at the intersection of beams S4 and 47, an RF echo wavelet 60 (FIG. 4b) corresponding to an echo source at axis position 50 is received by the noncompressing transducer 40. Meanwhile, transducer 38 is energized to emit a pulse and receive a corresponding echo from source 50. When transducer 38 is compressed a distance $\Delta y_i$, an elastic wave 55 travels through the tissue and diminishes asymptotically with range. The reference echo source 50 is moved slightly to position 51 along the beam axis 52. Second pulses are emitted from both transducers 38 and 40. A time shifted RF echo wavelet 62 (FIG. 4c) is received at noncompressing transducer 40, since the echo source 51 is now further from aperture 49.

If the angle between the beams is $\theta_1$, then $$\Delta t_{d,i} = \delta t_{d,i} \cos\theta_1. \quad (3)$$

The values of $\delta t_{d,i}$ so obtained are added to the denominator of Eq. (2) to result in an unbiased corrected estimator:

$$\hat{c}_u = \frac{2}{n} \sum_{i=1}^{n} \frac{\Delta y_i}{(\Delta t_i - \Delta t_{d,i}) + \delta t_{d,i} \cos\theta_1} \approx \hat{c}. \quad (4)$$

The method described so far estimates the speed of sound in a target body having a monolayer, which extends from the transducer aperture to the depth of interest. The method of the present invention may be extended to allow local estimation of sound speed in layered media, where each layer may, in general, have a different sound speed. The procedure involves sequential estimation of the speed of sound in progressively deeper layers.

Figure 5:
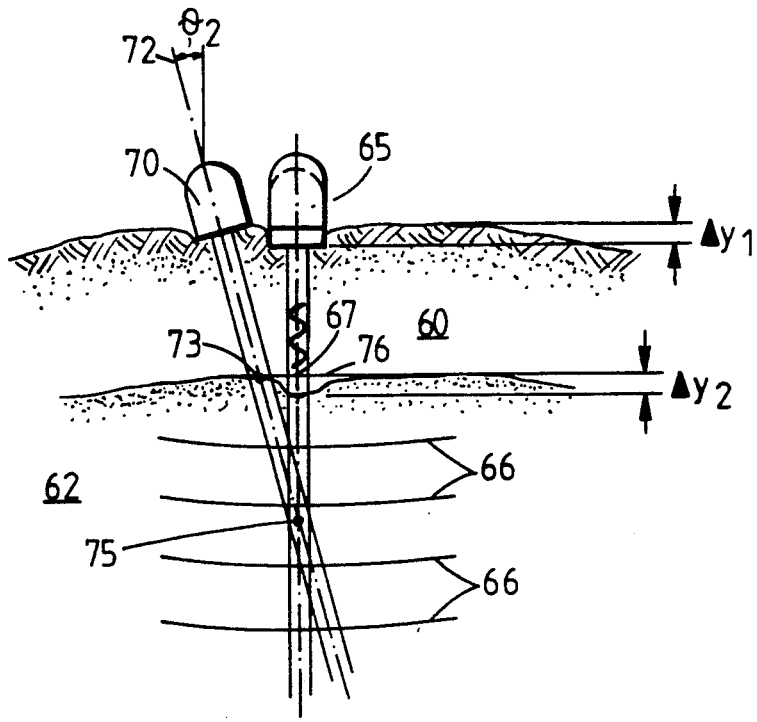
FIG. 5 shows an embodiment of the invention where two transducers are used to interrogate multiple tissue layers.

Turning now to FIG. 5, the estimate of the speed of sound in the first layer 60, $\hat{c}_{u1}$, is determined by applying the basic procedure to this layer whereby the boundary between the layers 67 is used as the echo feature. The speed of sound $\hat{c}_{u2}$ in the second layer 62 is determined by aiming transducers 65 and 70 at an angle 72 of $\theta_2$ at an echo source 75 in the second layer 62. Selection of the echo source is based upon the same criteria employed in the basic procedure outlined above. The undesired temporal shifts at 67 of the distal margin of the first layer 60 now become the forcing functions for the second layer 62, i.e., the spatial compressions imparted on the second layer are $$\Delta y_{2,i} = c_{u1} \delta t_{d1,i} \cos\theta_1 \quad (5a)$$

Advantageously, the quantities of $\Delta y_{2,i}$ may be estimated as $$\widehat{\Delta y}_{2,i} = \Delta y_{2,i} - \hat{c}_{u,1}(\Delta t_{1,i} - \Delta t_{1d,i}) \quad (5b)$$

Again, the minute displacements of the echo source 75 due to elastic wave 66 in the region of beam intersection appear as time shifts $\delta t_{d2,i} \cos\theta_2$ in one acquired RF signal plot. Applying equations (4) and (5a) to second layer 62 and temporarily assuming no displacement of the boundary 73 interrogated by the beam of the noncompressing transducer as shown in FIG. 5, we get:

$$\hat{c}_{u2} = \frac{2}{n} \sum_{i=1}^{n} \frac{\widehat{\Delta y}_{2,i}}{(\Delta t_{2,i} - \Delta t_{d2,i}) + \delta t_{d2,i} \cos\theta_2} \quad (6a)$$

$$2\frac{\hat{c}_{u1}}{n} \sum_{i=1}^{n} \frac{\delta t_{d1,i} \cos\theta_1}{(\Delta t_{2,i} - \Delta t_{d2,i}) + \delta t_{d2,i} \cos\theta_2}, \quad (6b)$$

$$\text{with } \hat{c}_{u1} = \frac{2}{n} \sum_{i=1}^{n} \frac{\Delta y_{1,i}}{(\Delta t_{1,i} - \Delta t_{d1,i}) + \delta t_{d1,i} \cos\theta_1}. \quad (7)$$

The quantities ($\Delta t_{2,i} - \Delta t_{d2,i}$) in eq. (6) are now measured as the time shift of the echo feature in the second layer before and after each compression, with respect to the boundary echo.

A slight complication arises in the approach of eqs. (6) and (7) if the region of the boundary 73 between first and second layers 60 and 62 that intersects the noncompressing beam is compressed as well. The assumption being eq. (6) has been that such compression does not occur. If such compression occurs and if it is of the same magnitude as the compression at 67 seen by the compressing transducer, then no additional useful information is gained by the noncompressing transducer over that which is available from the compressing transducer. In general, however, the compression of region 73 of the boundary will be non-zero, but less than the compression of the boundary region 67 that is under the compressing transducer. We observe that additional time delays (or advances) will be detected by the noncompressing transducer due to the motions of the boundary, where in a region of small boundary displacements $\delta\delta y_{d1,i}$ the speed of sound changes from $c_{u2}$ to $c_{u1}$. These measurable differences in the arrival time of the echoes from within the second layer due to this boundary displacement are given as $$\delta\delta t_{d2,i} = \widehat{\delta\delta y}_{d1,i} \left[ \frac{1}{\hat{c}_{u1}} - \frac{1}{\hat{c}_{u2}} \right], \quad (8)$$

and the quantity $\delta\delta y_{d1,i}$ can be estimated in a similar fashion to eq. (5a) as $$\widehat{\delta\delta y}_{d1,i} = \hat{c}_{u1} \delta\delta t_{d1,i} \quad (9)$$

where $\delta\delta t_{d1,i}$ is the measurable additional delay in the arrival time of the boundary echo at the noncompressing transducer. Combining eq. (8) and (9) yields $$\delta\delta t_{d2,i} = \hat{c}_{u1} \delta\delta t_{d1,i} \left[ \frac{1}{\hat{c}_{u1}} - \frac{1}{\hat{c}_{u2}} \right] \quad (10)$$

$$= \delta\delta t_{d1,i} \left[ 1 - \frac{\hat{c}_{u1}}{\hat{c}_{u2}} \right].$$

Adding this term to eq. (6) we get $$\hat{c}_{u2} = \frac{2}{n} \sum_{i=1}^{n} \frac{\hat{c}_{u1} \delta t_{d1,i} \cos\theta_1}{[\Delta t_{2,i} - \Delta t_{d2,i}] + [\delta t_{d2,i} \cos\theta_2 - \delta\delta t_{d2,i}]} \quad (11)$$

$$= \frac{2\hat{c}_{u1}}{n} \sum_{i=1}^{n} \frac{\delta t_{d1,i} \cos\theta_1}{[\Delta t_{2,i} - \Delta t_{d2,i}] - [\delta\delta t_{d2,i} - \delta t_{d2,i} \cos\theta_2]},$$

where $t_{d2,i}$ is given by eq. (10).

Since $\Delta t_{d2,i} = \delta t_{d1,i} \cos\theta_2$, the ability to solve eq. (11) relies on the inequality $$\Delta t_{2,i} - \delta\delta t_{d2,i} \neq 0. \quad (12)$$

This condition will hold true only if the boundary displacements seen by both transducers are unequal. This can usually be accomplished by properly separating the transducers. Given that the inequality of eq. (12) holds, equations (10) and (11) constitute a system of two equations with two unknowns, $C_{u1}$ and $C_{u2}$; the speed of sound in the deeper layer is estimated from knowledge of the speed of sound in the preceding layer and from some of the measured echo time delays. The layered regions are selected based upon the differential compressibility from front to back. Thus, in highly compressible tissue, the selected layers can be relatively thin, e.g., about 1 cm. For tissue regions that are not very compressible, the selected layers are thicker to help insure that sufficient differential compressibility is obtained for meaningful changes in signal path.

Although the apparatus and method of this invention have been described in relation to clinical diagnosis, this should be understood not to be a limiting factor on the utility of the invention. To the contrary, the present invention has utility in any area in which the speed of sound of organic tissue may be desired. For example, the present invention may be used in forensics, tissue characterization studies, veterinary medicine, laboratory experiments, and industrial applications. Also, the present techniques may be employed to any materials that are capable of being physically compressed or displaced. That is, a material which is internally displaceable in response to pressure applied to the material.

The various aspects of the invention will appear more specifically in the following examples that are purely illustrative and should not be construed to limit the scope of the invention.

EXAMPLE 1

A water tank experiment was conducted to test the method in a single layer using a simulated tissue phantom. A 150 mm×150 mm×50 mm block of fine reticulated polyester sponge was placed in a beaker and distilled water was added to completely immerse it. The beaker was placed in a desiccator and laboratory vacuum ($\approx 0.5$ bar) was applied for approximately 15 minutes. Thereafter, the beaker was submerged in a 60 gal. distilled water tank and the sponge removed and placed on a ¼ in. polished stainless steel reflector. The sponge was allowed to reach temperature equilibrium of 37°±0.5° C. A reference value for the speed of sound in the sponge phantom was obtained using the method shown in FIGS. 1-3, with the difference that echoes from a steel plate at the bottom of the phantom were used as the reference wavelets.

To determine the speed of sound using the method of the present invention, the method shown in FIG. 4a was used. Matched 13 mm, 3.5 mHz transducers were used. The compressing transducer was moved into the sponge at 0.4 mm increments, 10 increments total, for a total compression of 4 mm. The noncompressing transducer was aimed at target regions at several depths in the sponge, and echoes were recorded from both transducers at each incremental motion. Both the biased and unbiased speeds of sound estimates were calculated.

Figure 7:
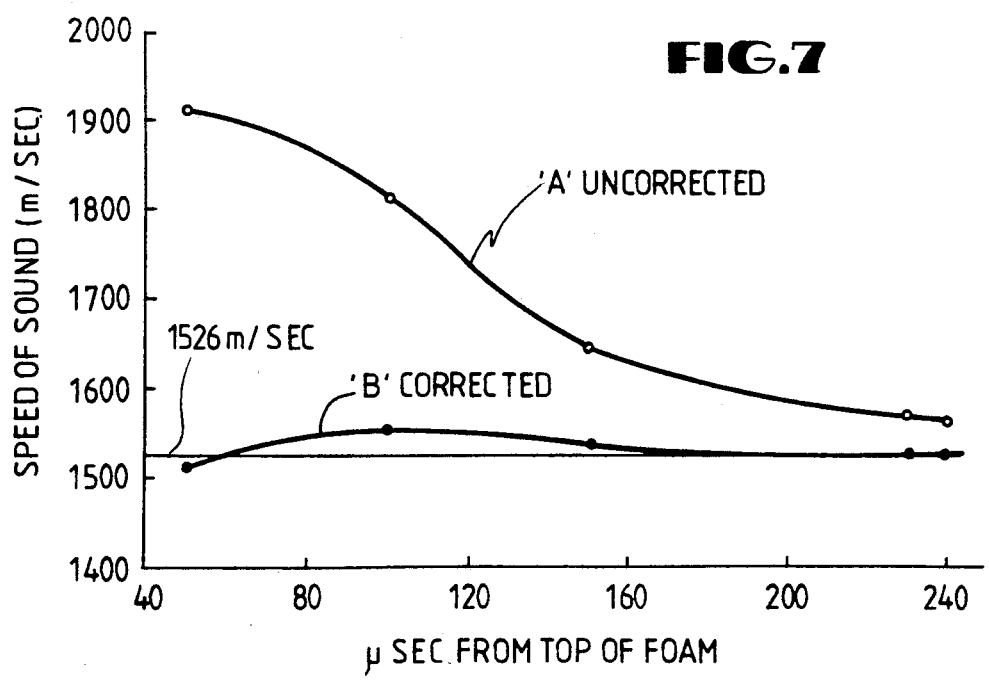
FIG. 7 is a plot comparing corrected and uncorrected speed of sound estimations in simulated tissue.

For the single-layer experiment, the reference value for the sponge and water phantom was found to be 1256±1 ms$^{-1}$. FIG. 7 summarizes the results for the single-layer experiment. Curve A shows the biased estimated speed of sound $c_b$ in the region of interest extending to different depths. Clearly, estimates that are made in regions close to the transducer are positively biased by up to 25 percent. This bias is expected from eq. (2). The bias in the estimate diminishes asymptotically toward the correct value, such that at a delay of 240 microseconds it amounts to about +2 percent. This is because the undesired distal compression of the region usually diminishes at greater depths in the sponge. Curve B shows the same data after corrections for the undesirable distal compressions, i.e., the quantity $c_u$ is within 1 percent or less of the value determined by direct measurement at all depths.

EXAMPLE 2

To test the ability of the present method to measure the speed of sound in an underlying tissue layer, a second foam phantom was constructed using the same material as before, but saturated in a water and Polyethylene Glycol 600 solution to elevate the speed of sound. For reference, the speeds of sound in the two phantoms were determined using the measurement technique described in Example 1. Next, the two phantoms were placed on a steel plate in water. To measure the sound speed in the second layer using the method of the present invention, the method shown in FIG. 5 was used. The noncompressing transducer was aimed at a target region in the second phantom, and the compressing transducer was moved 5 mm toward the plate, thereby compressing both phantoms. The change in arrival times of the echoes from the target region were recorded from both transducers. Multiple repetitions of the experiment were done and the average of the observations was used in the calculations.

In the two-layer experiment, the reference value for the speed of sound in the sponge in water and PEG-600 solution was 1589 ms$^{-1}$. A 5 mm motion of the compressing transducer resulted in a 1.08 mm translation of the boundary between the two phantoms, as observed with this transducer. The translation of the same boundary, but along the beam of the noncompressing transducer was 0.41 mm. The sound speed in the underlying phantom estimated using equation (6) was 1601 ms$^{-1}$, or +0.75 percent higher than the reference value.

Although the invention has been described with a certain degree of particularity, it is to be understood that the above description has been only by way of example. Numerous other changes will be apparent to those reading the specification without departing from the spirit and the scope of the invention as claimed.

What is claimed is:

1. A method for estimating sound velocity in a target medium, comprising the steps of:
   (A) acoustically coupling a first ultrasonic transducer to the surface of the medium;
   (B) energizing the first transducer to transmit a first ultrasonic signal from the surface of the medium along a path into the medium;
   (C) detecting the arrival time of a first echo signal of the first transmitted signal at the first transducer from a distal position along the path within the medium corresponding to a reference echo segment of the first echo signal;
   (D) displacing a portion of the medium proximal the first transducer sufficiency to change said arrival time while maintaining acoustic coupling between the first transducer and the medium;
   (E) energizing the first transducer;
   (F) detecting the changes arrival time; and (G) repeating steps (D) through (F), and determining the velocity of sound in the medium from the following equation:

$$c = \frac{2}{n} \sum_{i=1}^{n} \frac{\Delta Y_i}{\Delta t_i},$$

wherein c is the velocity of sound, n is the number of transducer displacement, $\Delta Y_i$ is the transducer displacement during the ith compression, and $\Delta t_i$ is the ith measured change in arrival time of the echo signal.

2. A method of estimating the velocity of sound in a target body with two ultrasonic transducers, each having a separate radiation axis, comprising the steps of:
 a) sonically coupling a first transducer to the surface of the body;
 b) selecting an echo source within said body on the radiation axis of said first transducer;
 c) sonically coupling a second transducer on the surface of the body and orienting it such that the radiation axis of the second transducer intersects the radiation axis of said first transducer at said echo source;
 d) detecting an arrival time at said first transducer for an echo originating from said echo source in response to a first ultrasonic pulse from said first transducer;
 e) detecting an arrival time at said second transducer for an echo originating from said echo source in response to a first ultrasonic pulse from said second transducer;
 f) translating said first transducer a known distance along its radiation axis toward said echo source by applying sufficient force to the body to compress the body between the first transducer and the echo source;
 g) detecting an arrival time at said first transducer for an echo originating from said echo source in response to a second ultrasonic pulse from said first transducer;
 h) detecting the arrival time at said second transducer for an echo originating from said echo source in response to a second ultrasonic pulse from said second transducer; and
 i) calculating the estimated velocity of sound in said tissue using the arrival times detected in steps d), e), g), and h), together with the translation distance of step f).

3. The method of claim 2 wherein said target body includes multiple layers, which comprises the further steps of:
 j) selecting a first echo source at a boundary between a first body layer and a second body layer;
 k) sonically coupling said first and second transducers on the surface of the body such that their respective radiation axes intersect at said first echo source;
 l) repeating steps d)-i) to determine the speed of sound in said first layer;
 m) selecting a second echo source within said second layer;
 n) reorienting said first and second transducers on the surface of the tissue such that their respective radiation axes intersect at said second echo source;
 o) detecting an arrival time at said first transducer for an echo originating from said second echo source in response to a third ultrasonic pulse from said first transducer;
 p) detecting an arrival time at said second transducer for an echo originating from said second echo source in response to a third ultrasonic pulse from said second transducer;
 q) translating said first transducer a known distance along its radiation axis toward said second echo source by applying sufficient force to the body to compress the body between the first transducer and the second echo source;
 r) detecting an arrival time at said first transducer for an echo originating from said second echo source in response to a fourth ultrasonic pulse from said first transducer;
 s) detecting an arrival time at said second transducer for an echo originating from said second echo source in response to a fourth ultrasonic pulse from said second transducer;
 t) calculating the estimated velocity of sound of said second layer using: (1) the arrival times measured in steps e) and h) as repeated in step l) together with the speed of sound of the first layer determined in step l), and (2) the arrival times detected in steps o), p), r), and s), together with the translation distance of step q).

4. A method of estimating the velocity of sound in a target body with one transducer, said transducer having a rotation axis, comprising the steps of:
 a) sonically coupling the transducer to the surface of the body;
 b) selecting an echo source within said body on the radiation axis of said transducer;
 c) detecting an arrival time at said transducer for an echo originating from said echo source in response to a first ultrasonic pulse from said transducer;
 d) translating said transducer a known distance along its radiation axis towards said echo source by applying sufficient force to the body to compress the body between the transducer and the echo source;
 e) detecting an arrival time at said transducer for an echo originating from said echo source in response to a second ultrasonic pulse from said transducer such that said echo originates from said echo source prior to displacement of the echo source by a compression wave associated with the tissue compression in step d); and
 f) calculating the estimated velocity of sound in said body using the arrival times measured in steps c) and e), together with the translation distance of step d).

5. The method of claim 4 wherein said target body includes multiple layers, which comprises the further steps of:
 g) selecting a first echo source at a boundary between a first body layer and a second body layer on the radiation axis of said transducer;
 h) repeating steps c)-f) to determine the speed of sound in said first layer;
 i) selecting a second echo source within said second body layer on the radiation axis of said transducer;
 j) detecting an arrival time at said transducer for an echo originating from said second echo source in response to a third ultrasonic pulse from said transducer;
 k) translating said transducer a known distance along its radiation axis towards said second echo source by applying sufficient force to the body to compress the body between the transducer and the second echo source;

l) detecting an arrival time at said transducer for an echo originating from said first echo source in response to a fourth ultrasonic pulse from said transducer such that said echo originates from said first echo source after the arrival of a compression wave associated with the tissue compression of step k);

m) detecting an arrival time at said transducer for an echo originating from said second echo source in response to said fourth ultrasonic pulse such that said echo originates from said second echo source before the arrival of said compression wave associated with the tissue compression of step k);

n) calculating the estimated velocity of sound in said second layer using: (1) the arrival times measured in step c) and e) as repeated in step h), together with the speed of sound of the first layer determined in step h), and (2) the arrival times measured in steps j), l) and m), together with the translation distance of step k).

* * * * *